(12) United States Patent
Fikes

(10) Patent No.: US 8,413,861 B2
(45) Date of Patent: Apr. 9, 2013

(54) GARMENT DONNER AND DOFFER

(76) Inventor: Raymond Fikes, Fountain Hills, AZ (US)

(*) Notice: Subject to any disclaimer, the term of this patent is extended or adjusted under 35 U.S.C. 154(b) by 217 days.

(21) Appl. No.: 12/964,953

(22) Filed: Dec. 10, 2010

(65) Prior Publication Data

US 2011/0139835 A1 Jun. 16, 2011

Related U.S. Application Data

(60) Provisional application No. 61/284,128, filed on Dec. 14, 2009.

(51) Int. Cl.
*A47G 25/90* (2006.01)
*A47G 25/00* (2006.01)

(52) U.S. Cl.
USPC .......................................................... 223/111

(58) Field of Classification Search ............. 223/111, 223/112
See application file for complete search history.

(56) References Cited

U.S. PATENT DOCUMENTS

| | | | |
|---|---|---|---|
| 2,038,840 A * | 4/1936 | Hall | 29/235 |
| 4,107,509 A | 8/1978 | Scher et al. | |
| 4,153,054 A * | 5/1979 | Boone | 128/856 |
| D267,428 S | 12/1982 | Christensen et al. | |
| 4,566,436 A | 1/1986 | Loefqvist | |
| 4,677,970 A | 7/1987 | Green et al. | |
| 4,868,967 A | 9/1989 | Holt et al. | |
| 4,905,998 A | 3/1990 | Last | |
| 5,070,597 A | 12/1991 | Holt et al. | |
| 5,486,206 A | 1/1996 | Avery | |
| 5,800,490 A | 9/1998 | Patz et al. | |
| 5,843,145 A | 12/1998 | Brink | |
| 6,401,247 B1 | 6/2002 | Williams, IV | |
| 6,523,729 B1 | 2/2003 | Gardon-Mollard | |
| 6,536,636 B1 * | 3/2003 | McDonniel | 223/111 |
| 7,060,086 B2 | 6/2006 | Wilson et al. | |
| 7,290,290 B2 | 11/2007 | Treadway Fancher | |
| 7,496,969 B2 | 3/2009 | Pieczynski | |
| 7,621,944 B2 | 11/2009 | Wilson et al. | |
| 8,042,716 B2 * | 10/2011 | Lun | 223/111 |
| 2003/0135171 A1 | 7/2003 | Ingram et al. | |
| 2004/0149789 A1 * | 8/2004 | Landsberger et al. | 223/112 |
| 2005/0087573 A1 | 4/2005 | Unsworth | |
| 2007/0239238 A1 | 10/2007 | Nausid | |
| 2009/0120975 A1 | 5/2009 | Schoepe | |

FOREIGN PATENT DOCUMENTS

| | | |
|---|---|---|
| GB | 2407961 | 5/2005 |
| JP | 08154800 | 6/1996 |
| WO | WO 9202754 | 2/1992 |
| WO | WO2007085061 | 8/2007 |

OTHER PUBLICATIONS

International Search Report and Written Opinion dated Jul. 29, 2011, PCT/US2010/059822.

* cited by examiner

*Primary Examiner* — Ismael Izaguirre
(74) *Attorney, Agent, or Firm* — Adam R. Stephenson, Ltd.

(57) ABSTRACT

Principles of the present disclosure contemplate use of a flexible sleeve to aid in donning and doffing garments, for example compression garments. The compression garment may be rolled around the sleeve via an eversion process. The compression garment may be unrolled from the sleeve and onto a limb via a reverse eversion process. Likewise, the compression garment may be unrolled from around a limb and onto the sleeve via an eversion process. By utilizing an eversion-based approach, compression garments may be donned and/or doffed more quickly and easily.

15 Claims, 16 Drawing Sheets

GARMENT DONNER AND DOFFER

CROSS REFERENCE TO RELATED APPLICATIONS

This application is a non-provisional of U.S. Provisional No. 61/284,128 filed on Dec. 14, 2009 and entitled "FLUID STOCKING DONNER".

TECHNICAL FIELD

The present disclosure relates generally to applying and removing compression garments from a body.

BACKGROUND

Compression garments are pieces of clothing, such as socks, pantyhose, sleeves, and/or the like, made from an elastic material. Compression garments provide support to the underlying tissue. Such support is especially useful for people who have to stand for long periods, or people with poor circulation, as a post surgical procedure to prevent clotting, and for athletes. The garments can come in varying degrees of compression. The higher degrees of compression typically require a doctor's prescription. Compression garments worn on the legs can help prevent deep vein thrombosis and reduce swelling, especially while traveling.

However, applying or removing compression garments is difficult at best and can be impossible for elderly or physically challenged persons. The task is often very difficult even with the assistance of a caregiver such as a family member, nurse or nursing assistant. Improved mechanisms and techniques for applying and/or removing compression garments and/or other similar garments thus remain desirable.

SUMMARY

This disclosure relates to garment donning and doffing. In an exemplary embodiment, an apparatus for donning and doffing a compression garment comprises a sleeve configured with a first sleeve opening, a second sleeve opening, an inner surface and an outer surface. The first sleeve opening, the inner surface and the second sleeve opening cooperate to define a passage through the sleeve for a limb. The inner surface and the outer surface are formed of and defined by a continuous flexible material. The outer surface at the second sleeve opening is configured for contact with at least one opening of the compression garment such that the compression garment can be continuously everted throughout the sleeve until the end of the compression garment opposite the at least one opening abuts the first sleeve opening.

In another exemplary embodiment, a method for coupling a sleeve and a compression garment comprises placing a compression garment over a pole, everting a sleeve in a first direction along the pole such that the compression garment is located between the sleeve and the pole, tucking an end of the compression garment into the sleeve, and everting the sleeve along the pole in a second direction opposite the first direction to cause the compression garment to wrap around the sleeve.

In another exemplary embodiment, a method for donning a compression garment comprises providing a sleeve having a first sleeve opening, a second sleeve opening, an inner surface and an outer surface wherein the first sleeve opening, the inner surface and the second sleeve opening cooperate to define a passage through the sleeve for a limb. The inner surface and the outer surface being formed of a continuous flexible material. The method further comprises providing a compression garment having at least one opening at one end thereof, providing a pole extending from a surface, sliding the at least one opening over the pole until the compression garment is fully extended over the pole, placing the second sleeve opening on the pole opposite the surface, and sliding the sleeve over the pole whereby the continuous flexible material everts such that the inner surface becomes the outer surface at the second opening while the outer surface becomes the inner surface at the first opening. The method further comprises pulling the at least one opening into contact with the outer surface at the second sleeve opening once the sleeve reaches the at least one opening, lifting the sleeve away from the surface whereby the continuous flexible material everts such that the inner surface becomes the outer surface at the first opening while the outer surface becomes the inner surface at the second opening. The lifting continues until the compression garment is completely removed from the pole, the end of the compression garment opposite the at least one opening abutting the first opening. The method further comprises positioning the first sleeve opening over a patient's limb, rolling the sleeve up the patient's limb whereby the inner surface and the outer surface evert thereby leaving the compression garment on the limb, disengaging the at least one opening from the second sleeve opening, and rolling the sleeve back down the limb until removed from the limb.

In another exemplary embodiment, a method of doffing a compression garment from a limb comprises providing a sleeve having a first sleeve opening, a second sleeve opening, an inner surface and an outer surface wherein the first sleeve opening, the inner surface and the second sleeve opening cooperate to define a passage through the sleeve for a limb, the inner surface and the outer surface being formed of and defined by a continuous flexible material. The method further comprises placing the first sleeve opening on the limb, sliding the sleeve over the limb whereby the continuous flexible material everts such that the inner surface becomes the outer surface at the first opening while the outer surface becomes the inner surface at the second opening, pulling at least one opening of a the compression garment into contact with the outer surface at the first sleeve opening once the sleeve reaches the at least one opening, and lifting the sleeve away from the surface whereby the continuous flexible material everts such that the inner surface becomes the outer surface at the second sleeve opening while the outer surface becomes the inner surface at the first sleeve opening, the lifting continuing until the compression garment is completely removed from the limb, the end of the compression garment opposite the at least one opening abutting the second sleeve opening.

The contents of this summary section are provided only as a simplified introduction to the disclosure, and are not intended to be used to limit the scope of the appended claims.

BRIEF DESCRIPTION OF THE DRAWINGS

With reference to the following description, appended claims, and accompanying drawings:

DETAILED DESCRIPTION

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the present disclosure.

For the sake of brevity, conventional techniques for garment donning, doffing, manufacture, use, and/or the like may not be described in detail herein. Furthermore, the connecting lines shown in various figures contained herein are intended to represent exemplary functional relationships and/or physical and/or communicative couplings between various elements. It should be noted that many alternative or additional functional relationships, physical connections, and/or communicative relationships may be present in a practical garment donning and/or doffing system or device.

Compression garments are often difficult to don and doff, particularly for physically challenged patients. Additionally, due to the compressive forces exerted by the garment, the garments may disrupt bandages or other clothing or medical equipment underneath the compression garment during donning and/or doffing. Due to these and other difficulties, various therapeutic benefits of compression garments often remain unrealized, as patients and/or caregivers struggle with the difficulties of using these garments as intended. Often, a patient may forego wearing a compression garment entirely due to the difficulty of having the compression garment properly put in place and/or removed.

Figure 1:
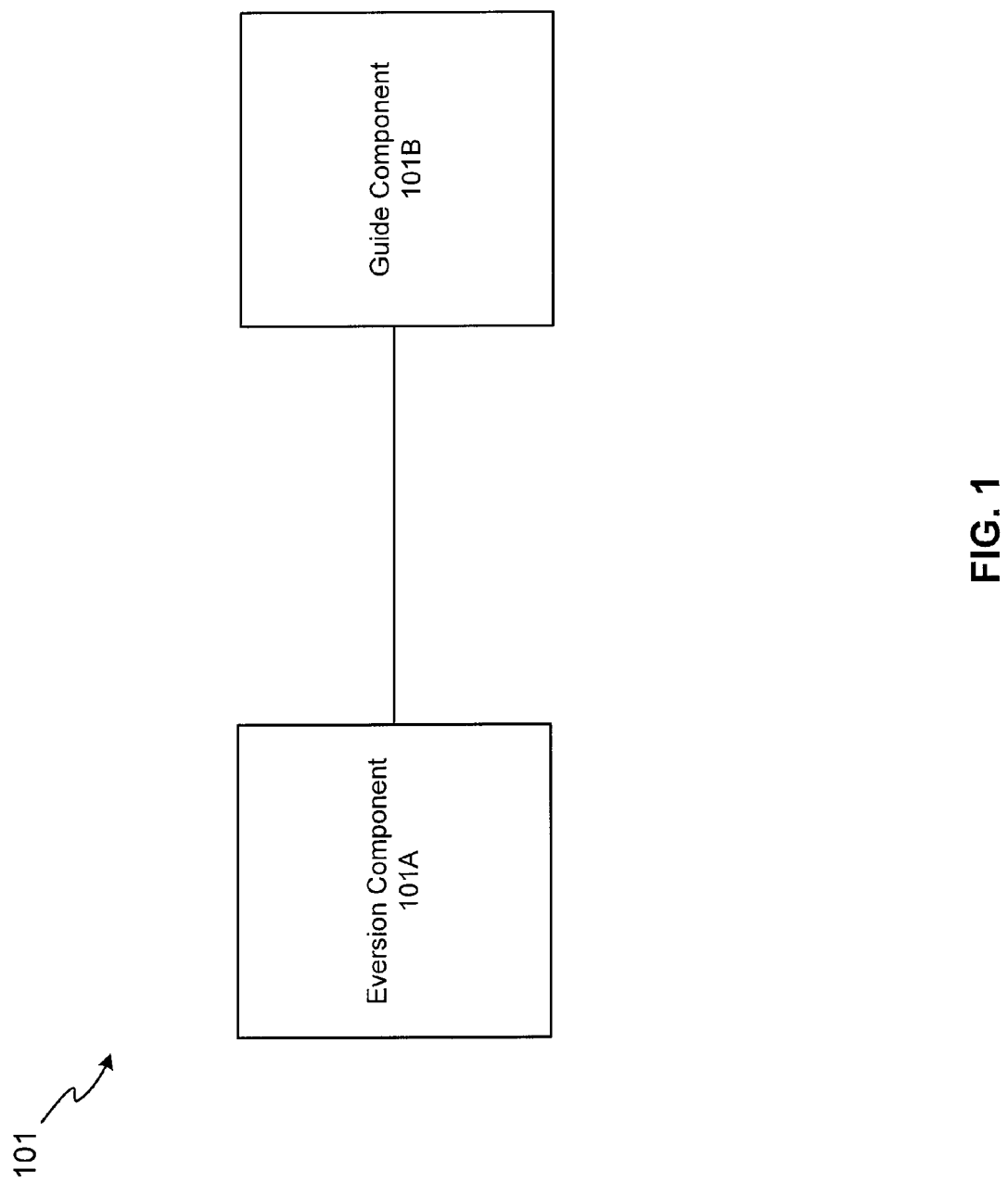
FIG. 1 illustrates a garment donning and/or doffing system in accordance with an exemplary embodiment.

In accordance with principles of the present disclosure, a garment donning system may be any system configured to facilitate donning and/or doffing of garments, for example compression garments. With reference now to FIG. 1, in an exemplary embodiment, a garment donning system 101 comprises an eversion component 101A and a guide component 101B. Eversion component 101A is configured to receive and/or release a compression garment via an eversion process (e.g., a process that turns a garment or other object at least partially "inside out"). Guide component 101B is configured to support and/or guide eversion component 101A and/or an associated compression garment during an eversion process.

Figure 2:
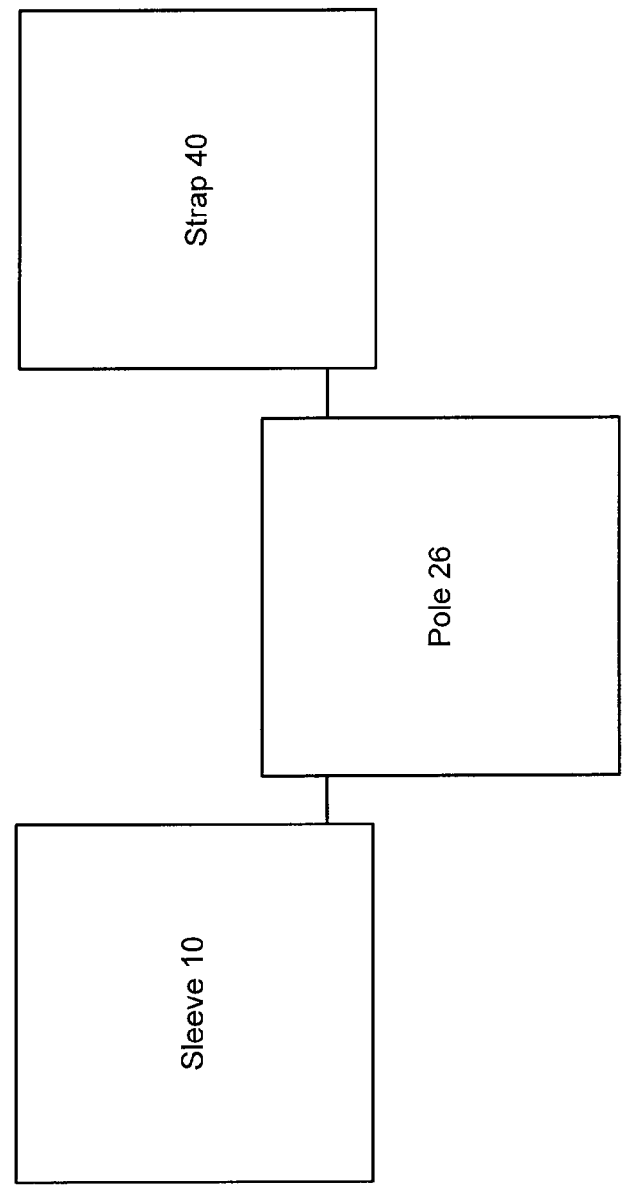
FIG. 2 illustrates a garment donning and/or doffing system in accordance with an exemplary embodiment.

Turning now to FIG. 2, in accordance with an exemplary embodiment a garment donning system 101 comprises an eversion component (e.g., sleeve 10) and a guide component (e.g., pole 26). In various exemplary embodiments, garment donning system 101 further comprises a strap 40. Sleeve 10 is configured to receive and/or release a compression garment via an eversion process. Pole 26 is configured to support and/or guide sleeve 10 and/or a compression garment during an eversion process. Strap 40 is configured to impart a force to cause eversion of sleeve 10, for example along pole 26.

Figure 6:
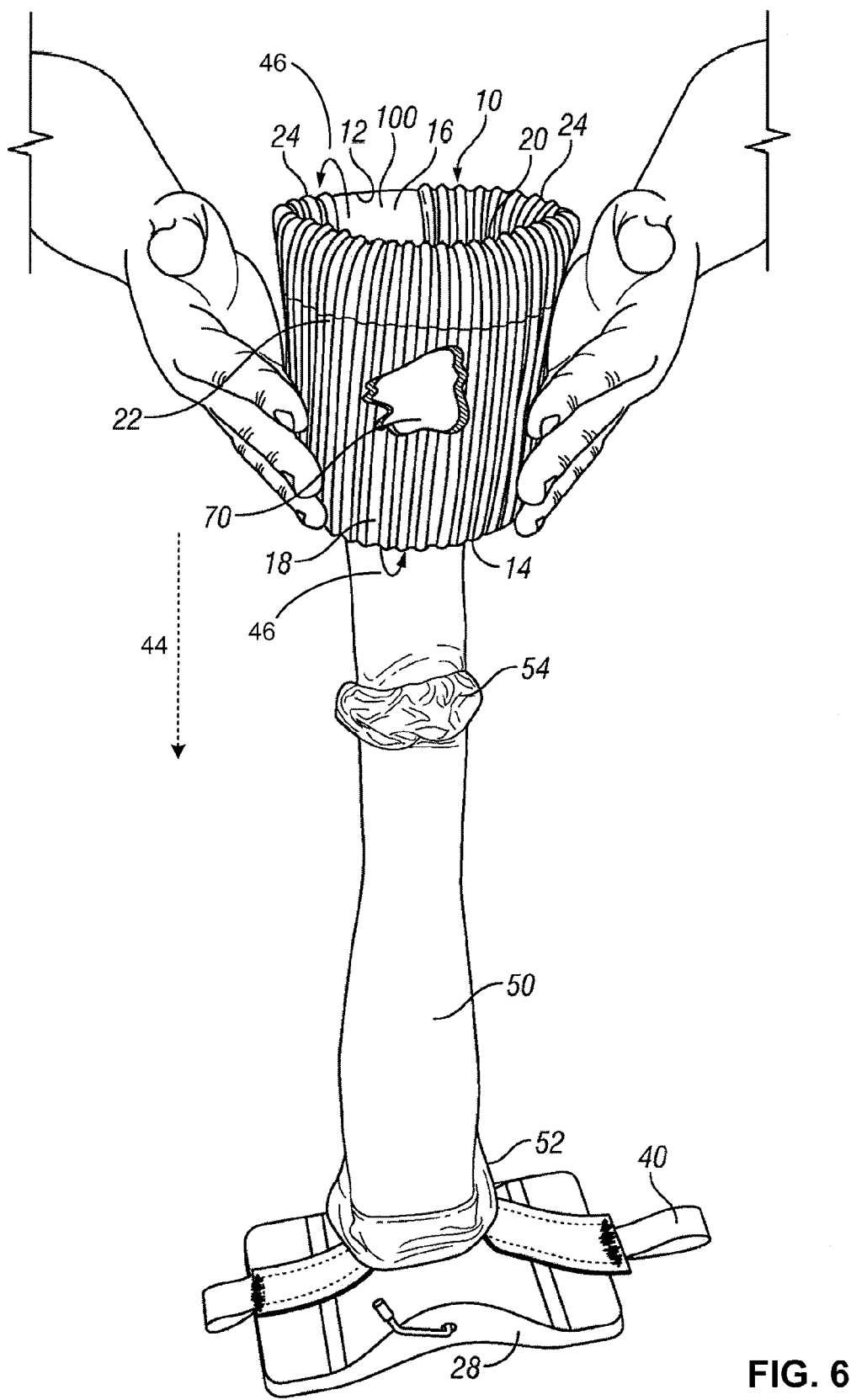
FIG. 6 illustrates a sleeve being positioned on the top of a pole, strap and compression stocking combination in accordance with an exemplary embodiment.

In various exemplary embodiments, with reference now to FIG. 6, sleeve 10 comprises a flexible structure having a generally toroidal topology. Moreover, sleeve 10 may comprise any suitable configuration such that sleeve 10 has an inner surface and an outer surface with two openings that define a passageway. In an exemplary embodiment, sleeve 10 is configured with a first sleeve opening 12, a second sleeve opening 14, an inner surface 16 and an outer surface 18. The first sleeve opening 12, the inner surface 16 and the second sleeve opening 14 cooperate to define a passage 20 through the sleeve 10. Passage 20 may be of suitable dimensions to allow a human limb to pass therethrough.

In various exemplary embodiments, the inner surface 16 and the outer surface 18 are formed of and defined by a continuous flexible material 22. Material 22 may comprise silicone, thermoplastic elastomers (e.g., styrenic block copolymers, polyolefin blends, elastomeric alloys, thermoplastic polyurethanes, thermoplastic copolyester, thermoplastic polyamides, and/or the like), rubber, or any other suitable flexible material or combination of materials. Flexible material 22 may also be a gel substance, of a specific shore and/or combination of shores, that comprises the entire sleeve 10 throughout. The continuous flexible material 22 is flexible enough to convey sleeve 10 over a limb.

In various exemplary embodiments, sleeve 10 further comprises a fluid 70 contained within continuous flexible material 22. Fluid 70 generally facilitates two purposes, one of hydraulics and one of lubrication. Fluid 70 may be water, solutions of water, oil, air, foams, urethane, silicone, lubricants, soaps, and/or any other material which may have desired properties. In addition to fluid 70, sleeve 10 may further be filled with beads, for example generally spherical glass beads or plastic beads, in suspension to aid in the reduction of friction between the inner surface 16 and the outer surface 18. In certain exemplary embodiments, sleeve 10 is configured with a fill and drain port 102 which allows refining of the size of passage 20 and for efficiency when traveling. In an exemplary embodiment, with momentary reference to FIG. 14, fill and drain port 102 comprises a syringe inserted into sleeve 10 at an angle. Flexible material 22 may be self-sealing around a syringe size hole. Moreover, fill and drain port 102 may comprise any suitable components and/or combination of components configured to allow addition of and/or removal of fluid or other material from sleeve 10. Moreover, in various exemplary embodiments sleeve 10 may be configured with a polymer coating, a flouropolymer coating (e.g., polytetraflouroethlyne "Teflon™", perfluoroalkoxy, and/or the like), parasilicone, and/or other suitable coatings in order to reduce and/or eliminate hydraulics or fluid.

In various exemplary embodiments, sleeve 10 may be filled with substances other than fluids, for example with beads, powders, petroleum jelly, and/or the like, or combinations of the same. In one exemplary embodiment, sleeve 10 is filled with powder. In another exemplary embodiment, sleeve 10 is filled with petroleum jelly. In another exemplary embodiment, sleeve 10 is filled with powder and petroleum jelly. The material or materials filling sleeve 10 and/or ratios may be selected according to the desired compression, the size of a patient's limb, and/or other suitable factors. By limiting the amount of fluid in sleeve 10, sleeve 10 may be configured to comply with requirements for commercial air travel, for example security requirements related to carry-on fluid volumes.

Figure 7:
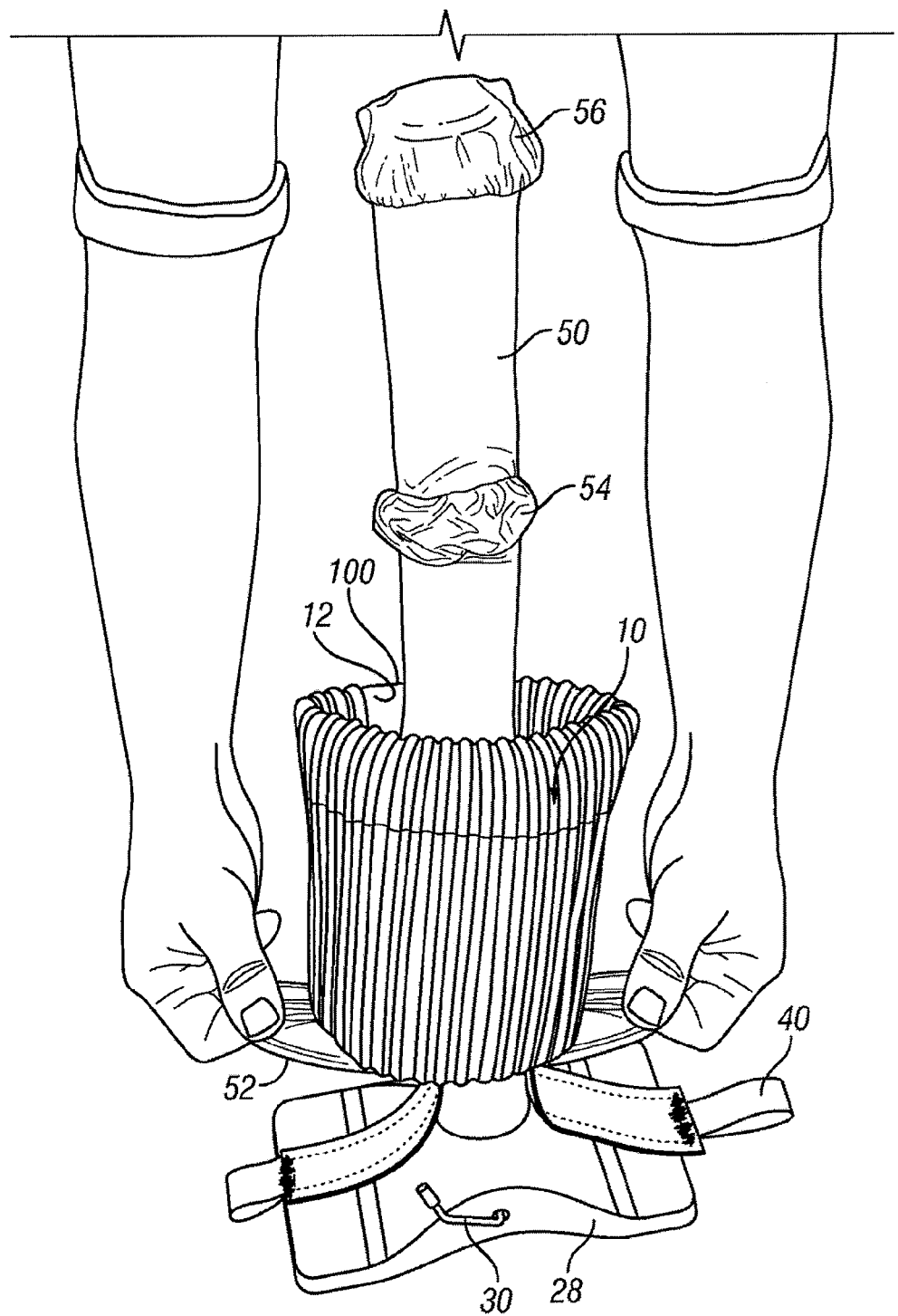
FIG. 7 illustrates the sleeve positioned at the bottom of the pole, strap and compression stocking with the user grasping opposing sides of the compression stocking opening in accordance with an exemplary embodiment.
Figure 8:
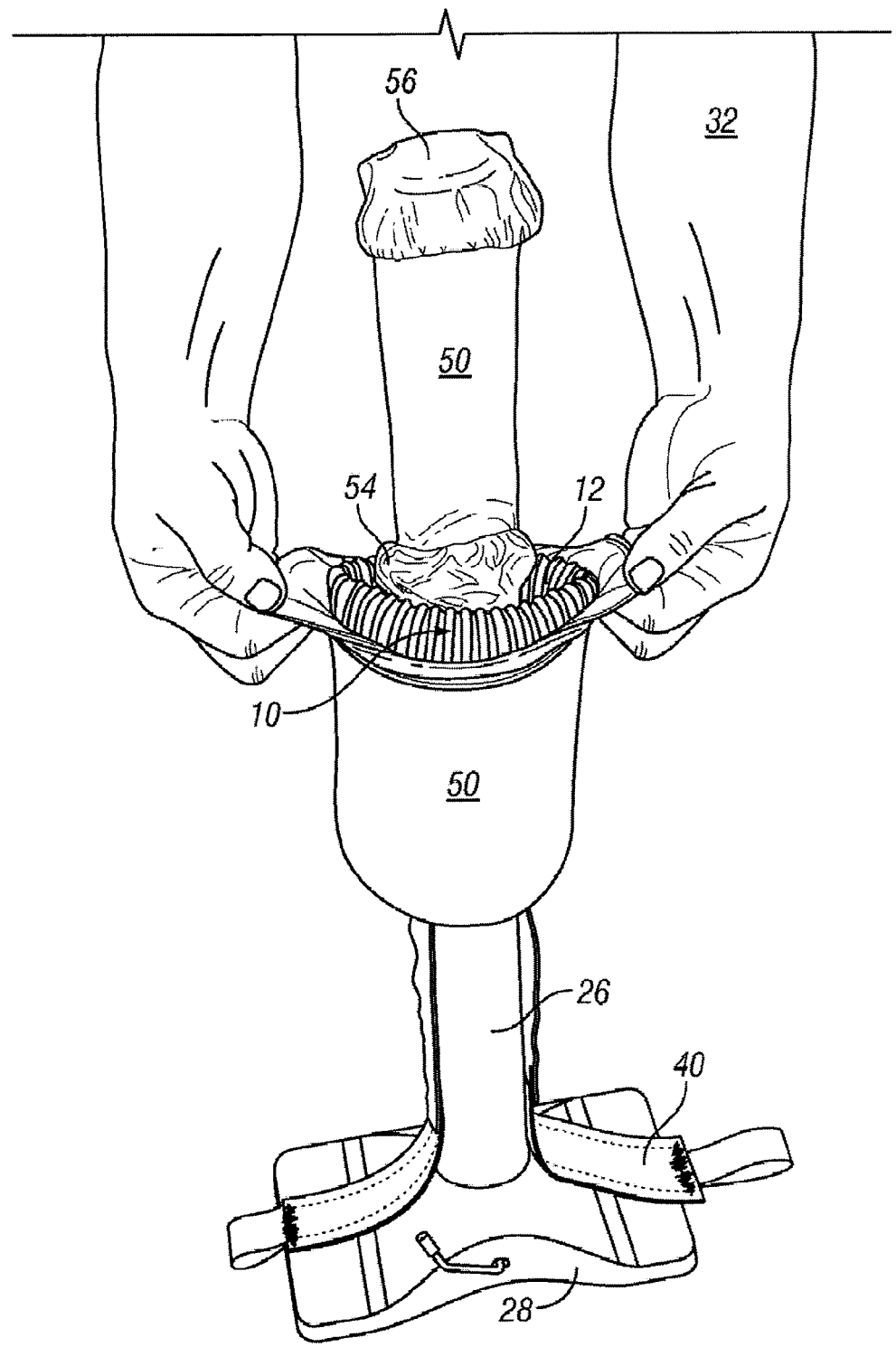
FIG. 8 illustrates a user lifting the compression stocking opening and the sleeve to about half way up the pole with the user folding the compression stocking opening into the upward sleeve opening in accordance with an exemplary embodiment.

In an exemplary embodiment, a plurality of longitudinally continuous and parallel raised lines 24 extend outwardly from inner surface 16 and outer surface 18. In some exemplary embodiments, lines 24 extend generally parallel to a central axis of the generally toroidal or other shape of sleeve 10 (for example, as illustrated in FIGS. 6 and 7). In other exemplary embodiments, lines 24 extend generally perpendicular to a central axis of the toroid. Moreover, lines 24 may extend in a diagonal manner, a curved manner, and/or any other suitable alignment and/or configuration, as desired.

In various exemplary embodiments, lines 24 are spaced between about 2 mm and about 24 mm away from one another. In various exemplary embodiments, lines 24 are raised between about 0.5 mm and about 5 mm above inner surface 16 and outer surface 18. Moreover, lines 24 may be spaced, raised, and/or otherwise configured in any suitable manner.

In an exemplary embodiment, continuing to reference FIG. 6, at least one of the plurality of longitudinally continuous and parallel lines 24 is a seam 100. In this exemplary embodiment, seam 100 extends in a direction generally parallel to lines 24. In other exemplary embodiments, seam 100 extends in a direction generally transverse to the lines 24. Moreover, seam 100 may be configured to facilitate conveyance of sleeve 10 over a limb. For example, in an exemplary embodiment seam 100 is configured to thicken sleeve 10 over the anterior aspect of a foot which has a shorter distance for travel than the posterior aspect of the foot, resulting in smoother conveyance over the foot. Sleeve 10 may be configured with a single seam 100; moreover, sleeve 10 may be configured with multiple seams 100. In an exemplary embodiment, sleeve 10 is formed by molding. Moreover, sleeve 10 may be formed via any suitable method, including seamless construction.

In an exemplary embodiment, sleeve 10 may be constructed with a longitudinal seam 100 by removing sleeve 10 from an original mold, and then sealing sleeve 10 end to end, for example via heat and/or adhesive. In an exemplary embodiment, a frame and/or clamp may be utilized to facilitate sealing of sleeve 10. Additionally, fluid 70 may be utilized as a parting agent and/or a stiffener when sealing sleeve 10. For example, sleeve 10 may be partially filled with fluid 70, and the ends of sleeve 10 may then be joined and clamped. Moreover, sleeve 10 may be formed, filled, and/or otherwise constructed in any suitable manner and/or by any suitable mechanism.

Figure 3:
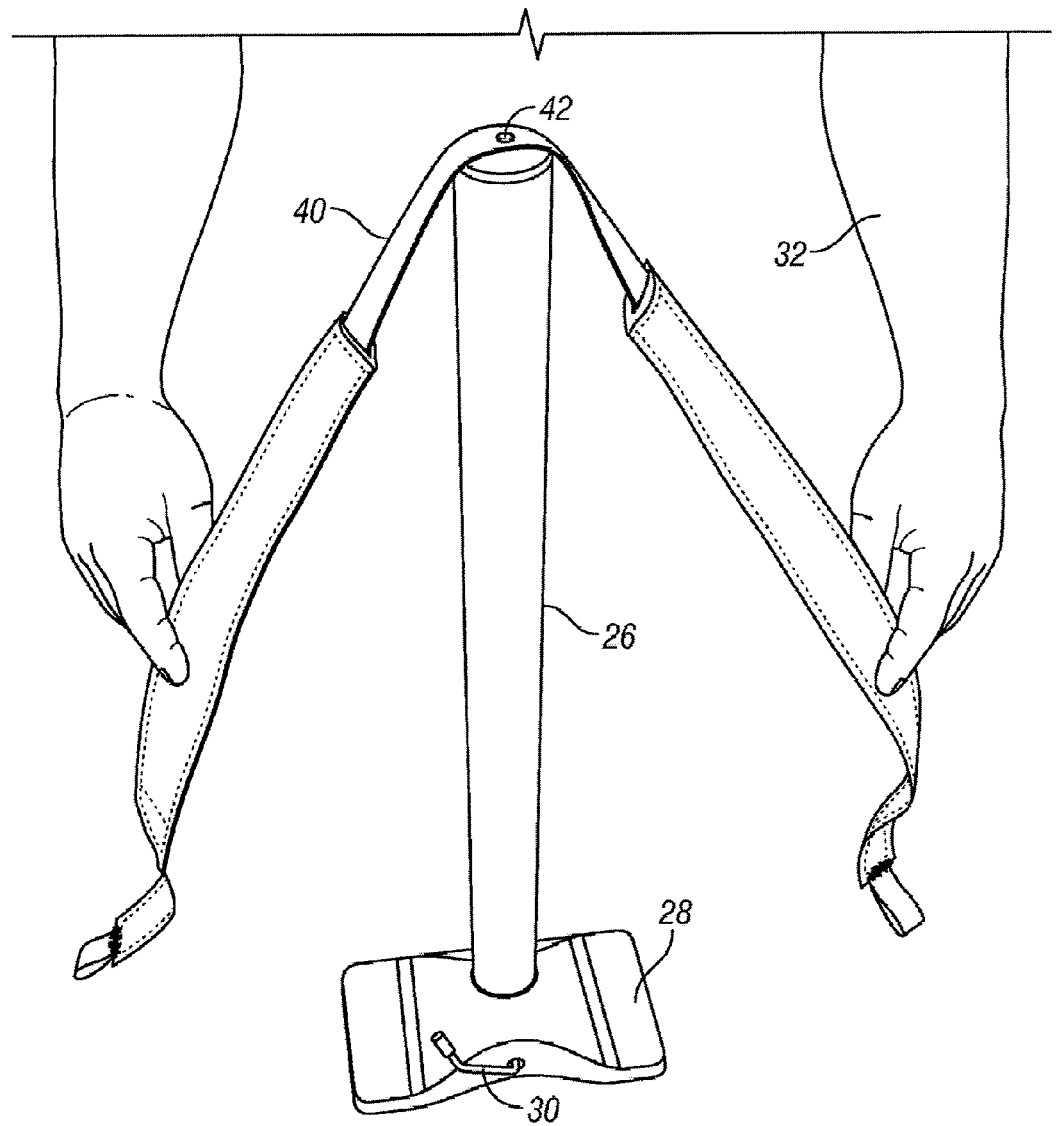
FIG. 3 illustrates a pole and strap combination in accordance with an exemplary embodiment.
Figure 4:
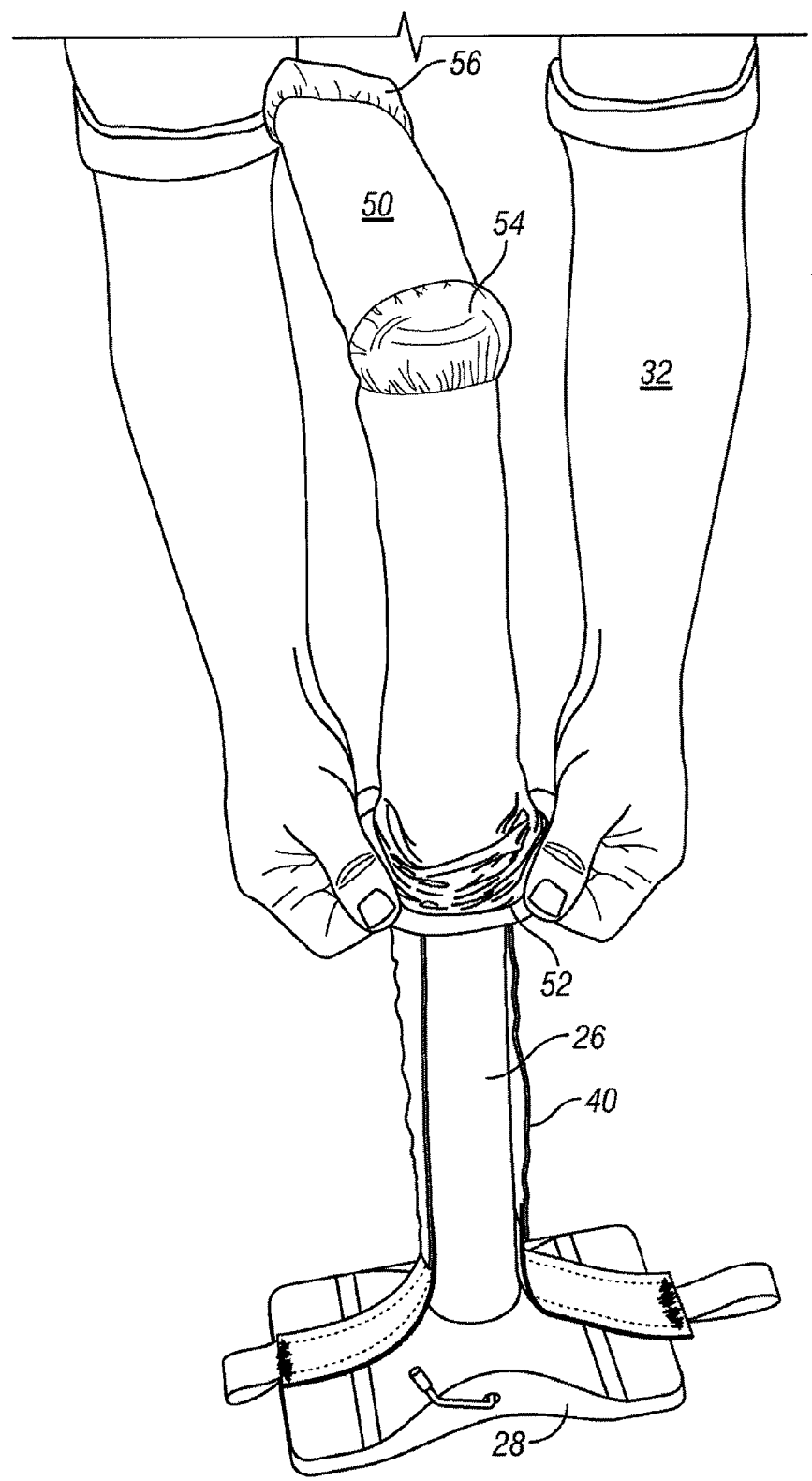
FIG. 4 illustrates a user sliding a compression stocking over a pole and strap combination in accordance with an exemplary embodiment.

In various exemplary embodiments, turning now to FIGS. 3 and 4, sleeve 10 may be utilized in connection with a pole 26. Pole 26 may comprise any suitable material, for example, metal, plastic, and/or the like. Pole 26 may be configured with any suitable length and/or other dimensions. In an exemplary embodiment, pole 26 has a length of between about 12 inches and about 48 inches. In various exemplary embodiments, pole 26 is configured to have a length greater than the length of a compression garment desired for use on a limb.

Pole 26 may be coupled to a base mount 28. In an exemplary embodiment, base mount 28 is configured with a suction lever 30. When base mount 28 is placed on a flat smooth surface, a user 32 may operate suction lever 30 in order to hold pole 26 in place. Moreover, any suitable components and/or methods for removably and/or permanently fixing pole 26 in place may be utilized. Additionally, pole 26 may be mounted to and/or formed from a location where pole 26 may be regularly utilized, for example at a nurse's station in a hospital, on a hospital bed frame, and/or the like.

Figure 16:
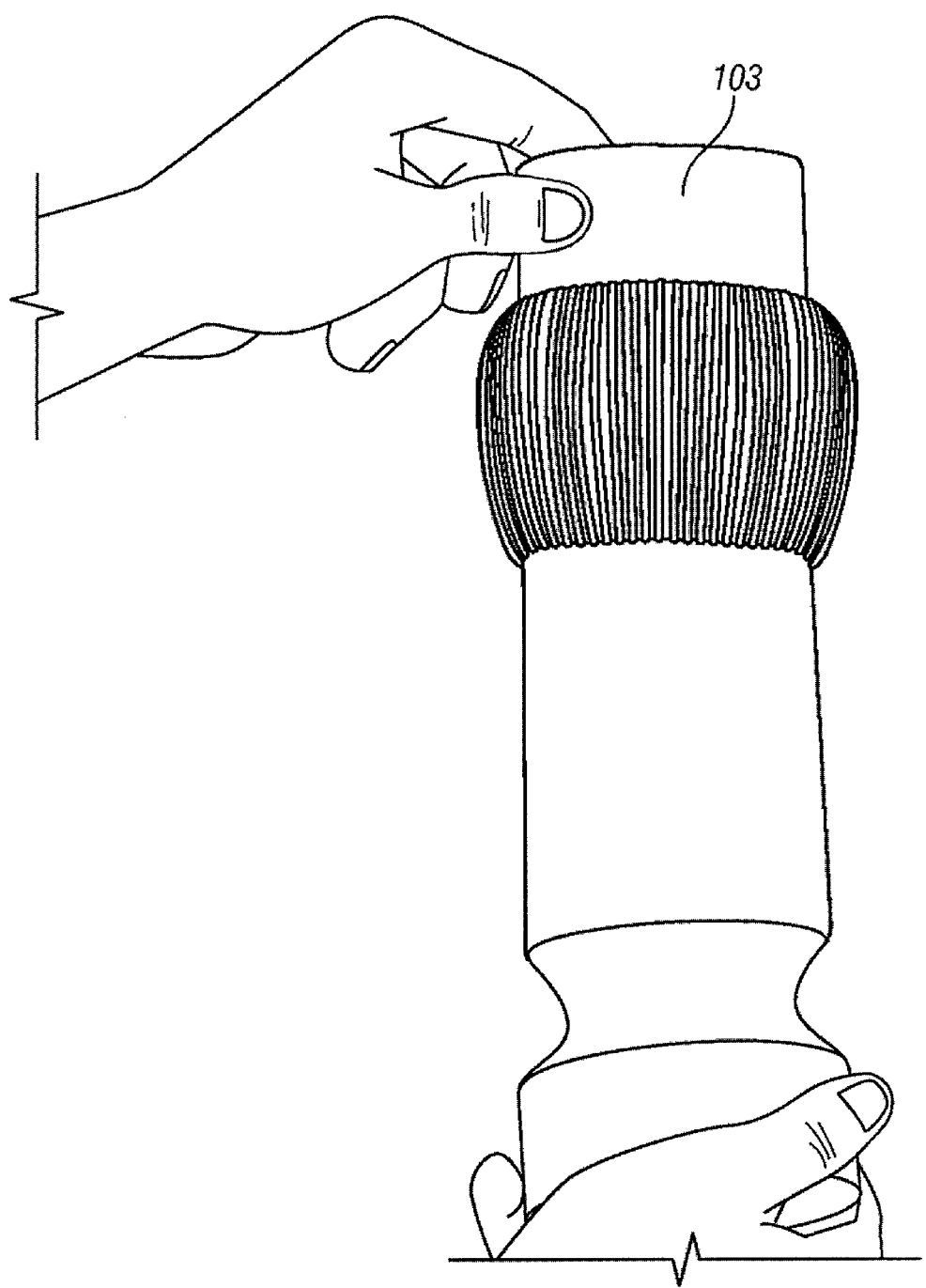
FIG. 16 illustrates an exemplary sleeve variant utilizing an optional skirt in accordance with an exemplary embodiment.

With momentary reference now to FIG. 16, in an exemplary embodiment sleeve 10 is configured with a skirt 103. Skirt 103 may be configured to function as a more elastic or less elastic portion of sleeve 10, making sleeve 10 more resistant or less resistant to eversion at a particular point. Moreover, skirt 103 may extend from the surface of sleeve 10. Skirt 103 may act as a retainer to aid in attaching compression garment 50 to sleeve 10. Moreover, skirt 103 may act to retain sleeve 10 in a desired location, for example by collaring limb 60 when the eversion direction of sleeve 10 is reversed. Any suitable number of skirts 103 may be provided on sleeve 10. Moreover, skirt 103 may be operative in a plane perpendicular to the direction of travel of sleeve 10 during the eversion process. Via use of skirt 103, sleeve 10 may be more effectively positioned and/or secured at a desired location, for example with respect to pole 26, a limb 60, and/or the like.

In an exemplary embodiment, returning now to FIGS. 3 and 4, pole 26 is coupled to a strap 40. Strap 40 may be centered on pole 26 opposite base unit 28. A fastener 42 such as a snap is provided to secure the center of strap 40 to pole 26 (for example, as illustrated in FIG. 3). Moreover, strap 40 may be coupled to pole 26 in any suitable location and/or via any suitable components or means. In various exemplary embodiments, strap 40 is of sufficient length such that each end 41 of strap 40 extends beyond the opposite end of pole 26 to which strap 40 is mounted. Stated another way, strap 40 is long enough to extend from limb opening 52 of compression stocking 50 when compression stocking 50 is slid fully over pole 26.

With reference now to FIG. 4, in various exemplary embodiments, a compression garment, for example a compression stocking 50, may be utilized in connection with sleeve 10 and pole 26. As will be appreciated, the use of compression stocking 50 is exemplary in nature, and various other compression garments and/or other garments may be utilized in accordance with principles of the present disclosure. In an exemplary embodiment, compression stocking 50 comprises a limb opening 52, a heel 54 and an enclosed toe 56.

Figure 5:
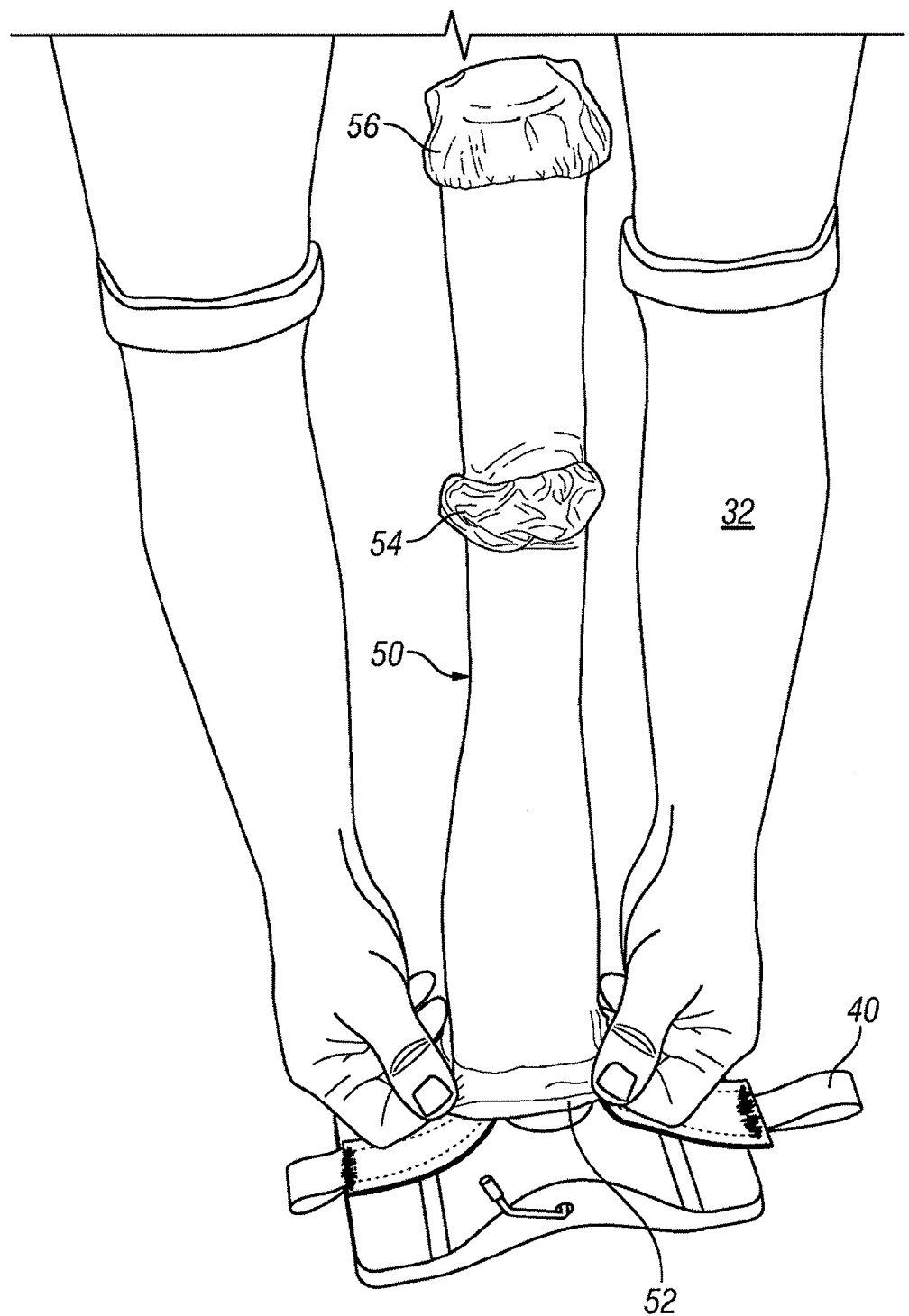
FIG. 5 illustrates a compression stocking fully in position on a pole and strap combination in accordance with an exemplary embodiment.

Compression stocking 50 may be "rolled around" sleeve 10 in order to form a suitable compression garment/sleeve assembly ready for installation on a limb. In an exemplary embodiment, with reference now to FIGS. 4-9, limb opening 52 of compression stocking 50 is slid over pole 26. Compression stocking 50 is slid until toe 56 encounters the end of pole 26 opposite base unit 28 (for example, as illustrated in FIG. 5). Moreover, compression stocking 50 may also be slid to any desired location, for example in the event compression stocking 50 is an open toed stocking. As can be appreciated, in the absence of pole 26, an arm, leg, or other suitable extension and/or projection may be utilized to provide similar function to that of pole 26.

In an exemplary embodiment, second opening 14 of sleeve 10 is placed on pole 26 opposite base unit 28 (for example, as illustrated in FIG. 6). As sleeve 10 slides down pole 26, material 22 does not move substantially along to pole 26. Rather, material 22 everts (e.g., turns "inside out"), whereby inner surface 16 remains generally stationary with respect to pole 26, but everts to become outer surface 18 at second opening 14, while outer surface 18 becomes inner surface 16 at first opening 12. As illustrated in FIG. 6, large arrow 44 shows the movement of sleeve 10 down pole 26 while smaller arrows 46 show the movement of continuous film of flexible material 22. In various exemplary embodiments, the diameter of passage 20 is equal to or smaller than the diameter of pole 26 to facilitate this movement.

In an exemplary embodiment, with momentary reference to FIG. 7, compression stocking 50 may be "wrapped around" sleeve 10. For example, once second opening 14 of sleeve 10 reaches the limb opening 52 of stocking 50, user 32 can pull opening 52 into contact with outer surface 18 of sleeve 10. With momentary reference to FIG. 8, once limb opening 52 is stretched over sleeve 10, it is lifted upward. This causes sleeve 10 to move up pole 26 with the eversion process as described above operating in the reverse direction. As sleeve 10 everts upward along pole 26, compression stocking 50 wraps around sleeve 10. Once limb opening 52 reaches first opening 12 of sleeve 10, it may be tucked into inner surface 16 (for example, as illustrated in FIG. 9).

Figure 9:
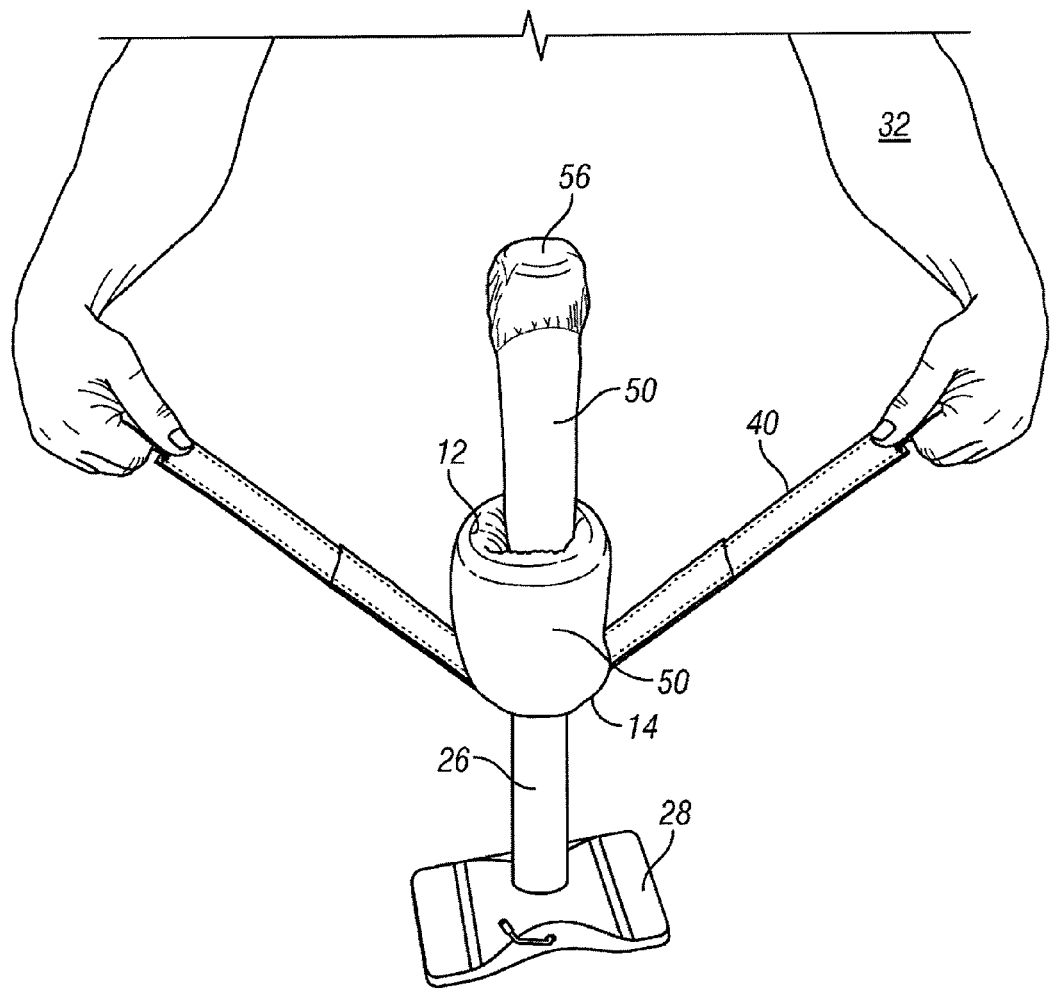
FIG. 9 illustrates a user pulling the strap upward to completely wrap the compression stocking about the sleeve in accordance with an exemplary embodiment.

In an exemplary embodiment, with continued reference to FIG. 9, once limb opening 52 is tucked into inner surface 16, user 32 may grasp straps 40 and provide a lifting force. Alternatively, user 32 may slide sleeve 10 upward manually. Responsive to the force, compression stocking 50 everts itself around inner surface 16 and 18 until it is removed from pole 26. At this point, stocking toe 56 will cover first opening 12 of sleeve 10, and the combined sleeve/stocking assembly disengages from pole 26. The sleeve/stocking assembly is now in a desirable configuration to facilitate simplified installation of compression stocking 50 onto a limb. Moreover, the number of revolutions or eversions that compression stocking 50 is encased in by this process can be changed by modifying where compression stocking 50 is tucked in the eversion process.

In various exemplary embodiments, sleeve 10 and compression stocking 50 may be configured separately. In other exemplary embodiments, sleeve 10 and compression stocking 50 may be pre-configured together as a rolled-up sleeve/stocking assembly, for example as described above, and then offered as a unit to consumers, medical professionals, and/or the like.

Figure 10:
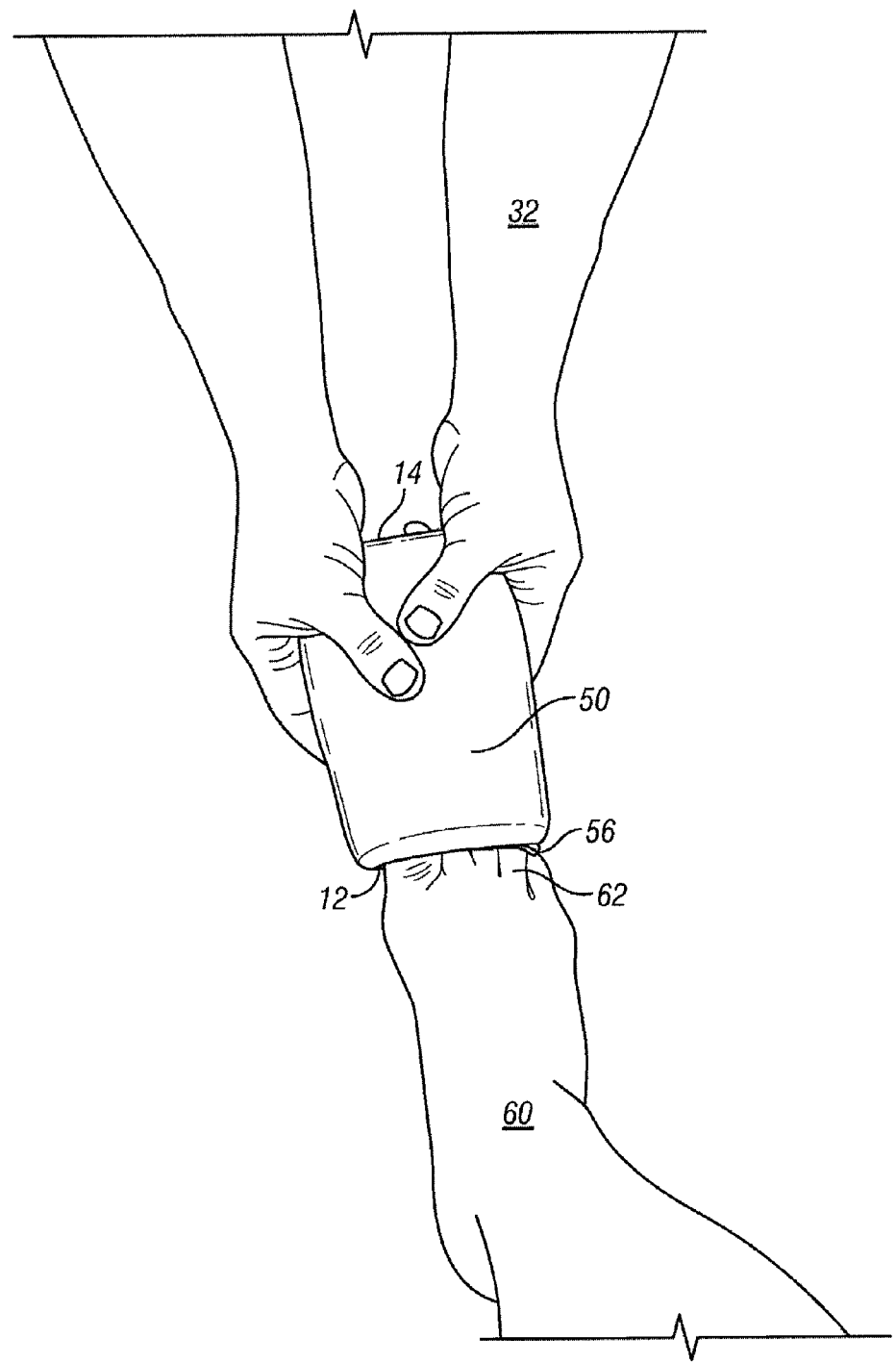
FIG. 10 illustrates a user placing the sleeve with compression stocking combination on the foot of a patient with the compression stocking toe corresponding to the patient's toes in accordance with an exemplary embodiment.
Figure 11:
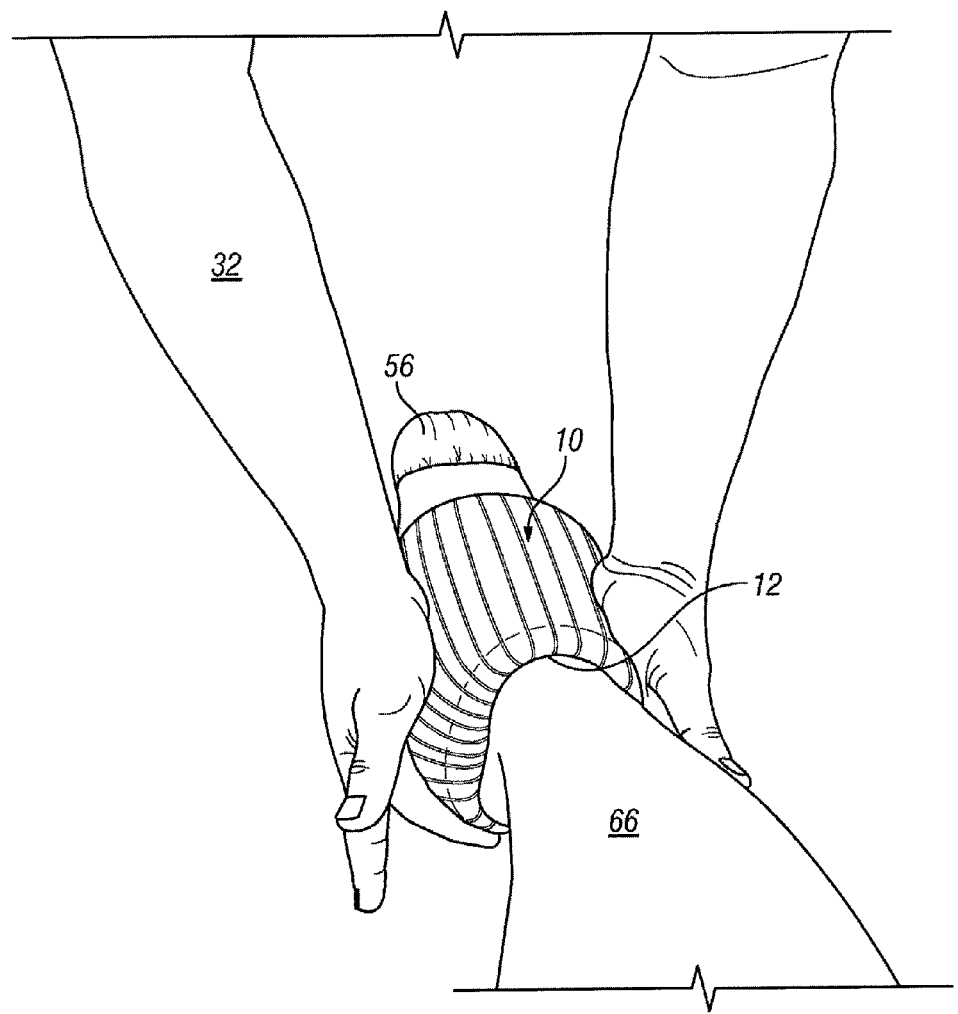
FIG. 11 illustrates a user rolling the sleeve and compression stocking combination up the leg of a patient in accordance with an exemplary embodiment.
Figure 12:
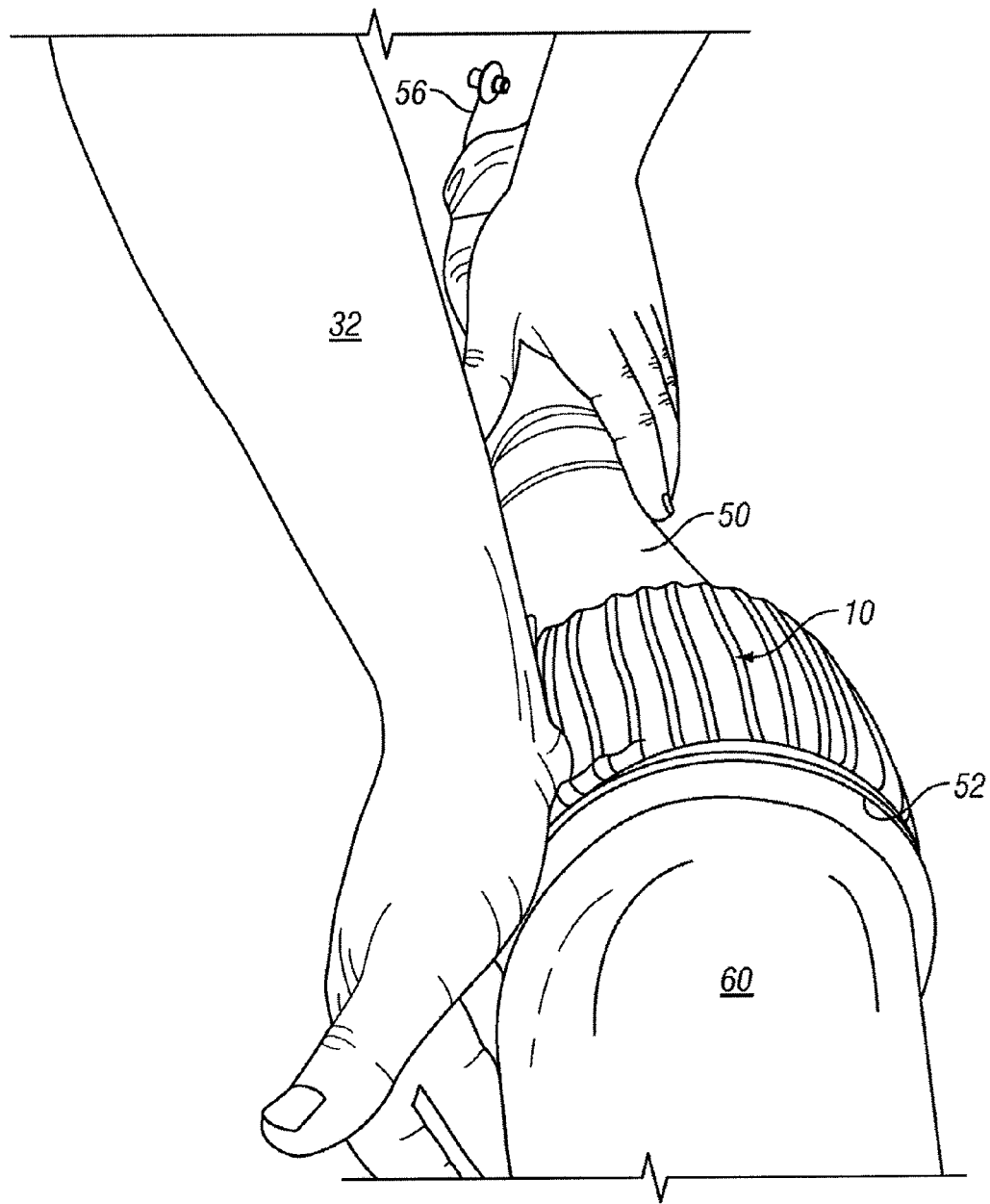
FIG. 12 illustrates a user positioning the sleeve and compression stocking combination at the knee of the patient in accordance with an exemplary embodiment.
Figure 13:
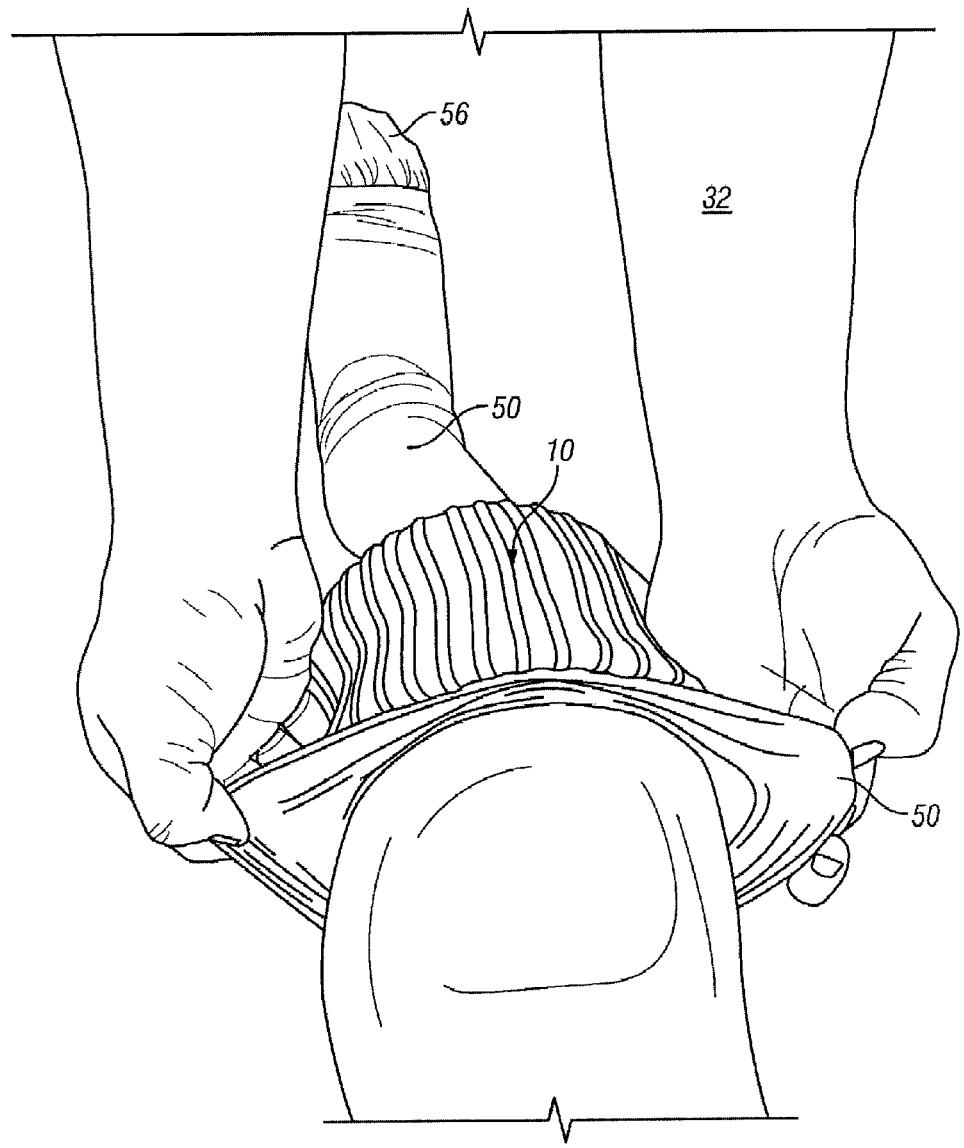
FIG. 13 illustrates a user disengaging the compression stocking opening from the limb in accordance with an exemplary embodiment.
Figure 14:
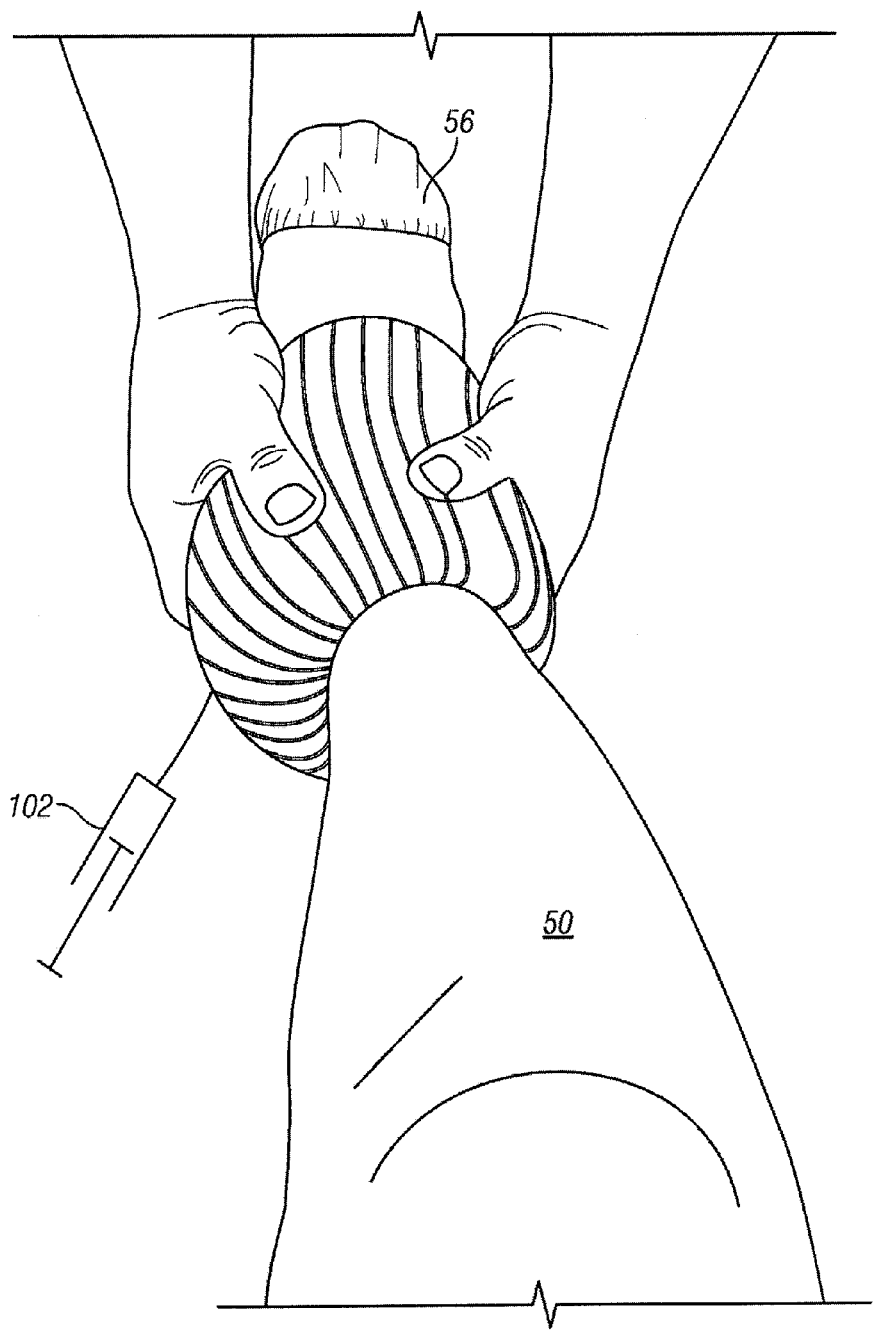
FIG. 14 illustrates a user removing the sleeve from the patient's leg and leaving the compression stocking on the patient's leg in accordance with an exemplary embodiment.
Figure 15:
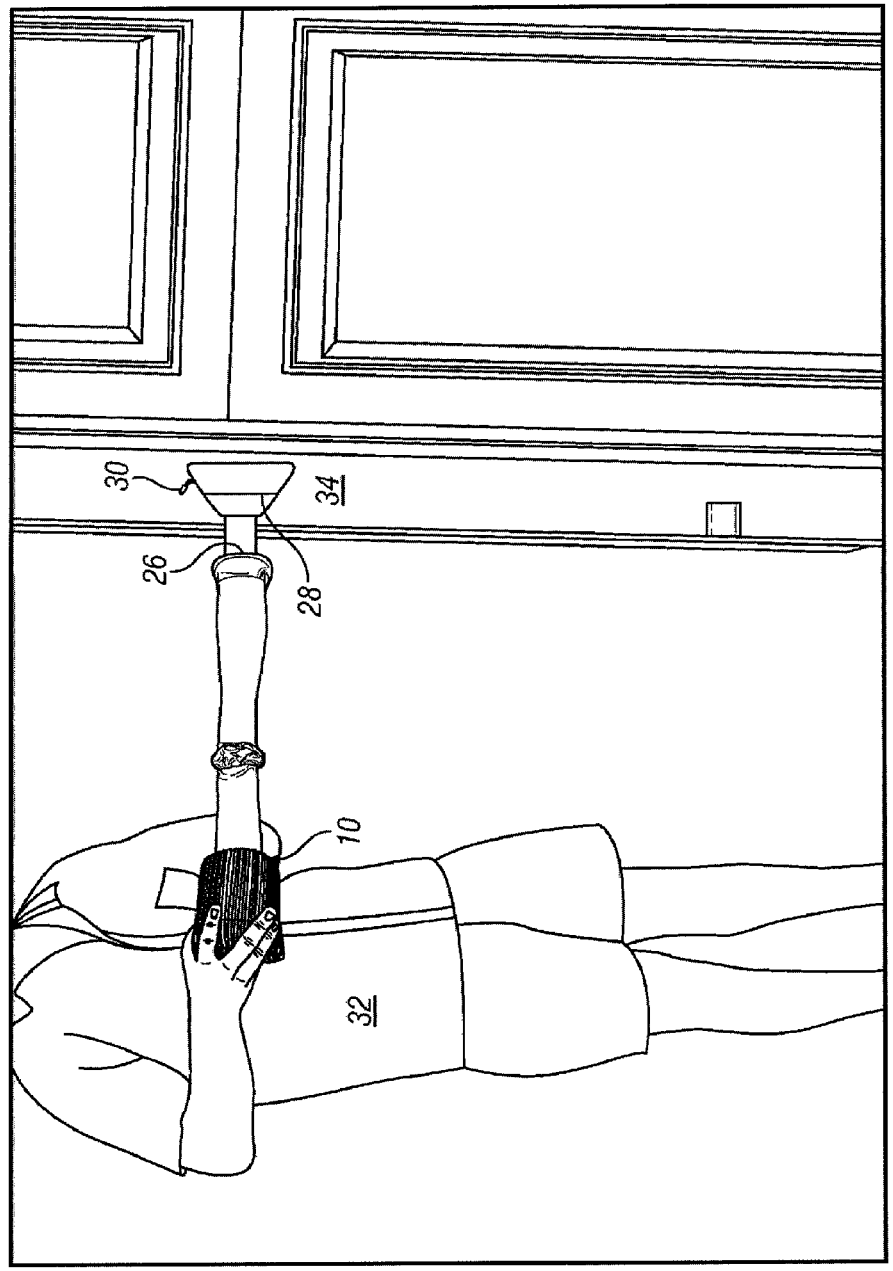
FIG. 15 illustrates use of a compression garment and sleeve in connection with a horizontal pole in accordance with an exemplary embodiment.

In various exemplary embodiments, a rolled-up sleeve/stocking assembly may be utilized to apply a compression garment to a limb and/or remove a compression garment from a limb. Stated generally, sleeve 10 may be considered to facilitate "rolling" a compression garment onto a limb (i.e. "donning"), and/or "unrolling" a compression garment off a limb (i.e., "doffing"). With reference now to FIGS. 10-13, in an exemplary embodiment compression stocking 50 may be applied to a limb, for example limb 60. Compression stocking 50 may be applied by a nurse, physical therapist, or other caregiver; alternatively, compression stocking 50 may be applied by a patient. To apply compression stocking 50, user 32 positions first opening 12 with stocking toe 56 over toes 62 of the patient's limb 60 (for example, as illustrated in FIG. 10). User 32 then rolls sleeve 10 up limb 60 (for example, as illustrated in FIG. 11). As sleeve 10 rolls up limb 60, inner surface 16 and outer surface 18 evert, causing compression stocking 50 to disengage from sleeve 10 and surround limb 60 (for example, as illustrated in FIGS. 12 and 13). Once sleeve 10 everts enough whereby limb opening 52 and second opening 14 are abutting, limb opening 52 is disengaged from sleeve 10 (for example, as illustrated in FIG. 13). At this point, sleeve 10 may be rolled back down limb 60, leaving limb 60 covered by compression stocking 50 (for example, as illustrated in FIG. 14).

In various exemplary embodiments, doffing of compression stocking 50 may be achieved via substantially a reversal of a donning process. In an exemplary embodiment, when compression stocking 50 is in place on a limb, compression stocking 50 may be removed from the limb, as follows: Sleeve 10 is rolled up limb 60 (for example, as illustrated in FIG. 14). Once second opening 14 and limb opening 52 abut, limb opening 52 is stretched to cover outer surface 18 adjacent second opening 14 (for example, as illustrated in FIGS. 12 and 13). Once limb opening 52 is in place, sleeve 10 is now rolled down limb 60 (for example, as illustrated in FIG. 11) and then completely removed from limb 60 (for example, as illustrated in FIG. 10). At this point, sleeve 10 and compression stocking 50 may again be in a desirable rolled-up sleeve/stocking assembly ready for re-donning on a limb.

In various exemplary embodiments, if sleeve 10 and compression stocking 50 are desired to be separated, pole 26 may be utilized. Moreover, it may be simpler to simply grasp toe 56 and then release sleeve 10. The weight of sleeve 10 can thus act to unroll compression stocking 50 from around sleeve 10.

In addition to use in donning and/or doffing garments, for example compression garments, sleeve 10 may be desirably utilized in connection with various medical procedures and/or therapies. For example, in various exemplary embodiments, sleeve 10 may be utilized in connection with edema management and/or decongestive therapy. Typically, physical therapists often treat patients with edema or swelling by massaging fluid back into tissue with their hands. In contrast, in an exemplary embodiment a physical therapist or other caregiver may utilize sleeve 10 for treatment of edema, for example by placing sleeve 10 over the hand of a patient, and then squeezing sleeve 10 as sleeve 10 is rolled slowly up the patient's arm. Because individual therapists have varying hand sizes and strength, utilization of sleeve 10 brings a first advantage of a standardized force to this discipline. It also allows for second advantage of a static variation, in that the therapist can release the force applied by them, and replace it with another sleeve 10 that causes the first sleeve 10 to lock in position and/or stay in place. The various sleeves 10 may be of varying shores and/or fluidity in order to provide a third advantage of a gradient pressure aspect on the limb.

Similarly, in various exemplary embodiments sleeve 10 may also be utilized for decongestive therapy. A common technique for decongestive therapy, for example to treat edema of a hand or arm, involves the caregiver holding the affected hand with one hand, and then using the caregiver's other hand to grasp the patient's wrist. The caregiver then repeatedly "milks" the edema away by slowly sliding this loose grip up the patient's arm. In contrast, in an exemplary embodiment a caregiver may utilize one or more sleeves 10, for example, two sleeves 10, to facilitate "milking" the edema away and allowing the caregiver's grip to slide up the arm of the patient.

In certain exemplary embodiments, sleeve 10 may be utilized in connection with therapeutic massage, relaxation massage, and/or the like. When utilized in connection with massage, sleeve 10 may be utilized to provide compressive forces to skin, muscle, connective tissue, lymphatic vessels, and/or any other suitable body parts in order to enhance function, stimulate blood flow, and/or promote relaxation. When sleeve 10 is utilized in connection with massage, sleeve 10 may be heated and/or cooled in order to enhance a desired result. Moreover, when sleeve 10 is utilized in connection with massage, sleeve 10 may be configured with various structures, external coatings, textures, and/or geometric features, for example in order to provide a desired pressure, tactile stimulation, or other physiological manipulation or stimulation to a massage patient.

In various exemplary embodiments, sleeve 10 may be at least partially filled with a material suitable for use as a heat pack and/or a cold pack. In this manner, sleeve 10 may be utilized to provide heat therapy and/or cold therapy to an affected area, for example in order to treat bruising, swelling, and/or the like. Moreover, skirt 103 may be utilized to retain sleeve 10 in a desired location, for example in order to facilitate transfer of therapeutic heat and/or cold to a target area.

In various exemplary embodiments, sleeve 10 is configured with a smooth surface lacking any lines 24. In these embodiments, sleeve 10 may comprise certain portions having a first coefficient of friction, and other portions having a second coefficient of friction different from the first coefficient of friction. Moreover, in various exemplary embodiments, sleeve 10 may be covered with an additional material, fabric, coating, and/or finish configured to either increase friction or decrease friction. In this manner, sleeve 10 may be configured to suitably interface with a variety of compression garments having varying frictional and/or material characteristics, as desired.

In certain exemplary embodiments, sleeve 10 may be configured with various trenches, zig-zags, and/or other surface geometries configured to allow sleeve 10 to expand and/or contract in an accordion-like manner. By configuring sleeve 10 in an expansible fashion, sleeve 10 may be better suited to compress the toe area of a compression garment 50, while still being able to expand sufficiently to evert around the greater circumferences associated with the upper portions of a limb, such as an upper leg.

In various exemplary embodiments, sleeve 10 may be integrated with and/or incorporated directly into a proximal aspect of compression garment 50. When donning and/or doffing compression garment 50, sleeve 10 may first be filled with fluid in order to facilitate the eversion process. Sleeve 10 may then be drained, for example while the patient wears compression garment 50, or after compression garment 50 has been removed from a limb. Additionally, when incorporated with a compression garment 50, sleeve 10 may comprise a sheet of gel incorporated into the proximal aspect of compression garment 50. When compression garment 50 is doffed, the sheet of gel rolls with and about compression garment 50, resulting in a similar combination of fluidity and garment layering as may be achieved with a separate sleeve 10. The sheet of gel may also be filled with fluid and/or drained, for example in order to aid in donning and doffing, to refine the size requirements for a specific limb to compression garment ratio, and/or the like.

In various exemplary embodiments disclosed herein, sleeve 10 is configured for use with compression garment 50. More broadly, sleeve 10 may be configured to convey any suitable generally tubular material onto a surface via an eversion process. Sleeve 10 may thus be sized, shaped, and/or configured in any appropriate manner, and the examples related to conveying a compression garment over a limb are provided by way of illustration and not of limitation.

Yet further, in various exemplary embodiments sleeve 10 may be utilized in a variety of industrial processes and apparatuses. For example: (i) sleeve 10 may be utilized in connection with gluing or affixing a material on a tubular or otherwise irregular shape when a conveyance of the material is warranted. Additionally, (ii) when sleeve 10 is encased, sleeve 10 can function as a powerful bearing mechanism. Yet further, (iii) when utilized with a strapping mechanism, sleeve 10 provides a reciprocal conveyance mechanism that is outstanding for traction and/or entrapment. For example, sleeve 10 may be conveyed onto a limb or object by rolling the outside, but as the straps are pulled from the inside, sleeve 10 generates a resultant force opposite to the direction of pull, resisting removal from the limb or object. Moreover, (iv) when encased in a structure where the two openings in sleeve 10 are affixed to the frame of the structure at opposite ends and one part of the structure is moved relative to the other, sleeve 10 generates a gripping force that rivals suction cups. Sleeve 10 could be used in industry to grasp, hold or move objects, and sleeve 10 may be particularly well suited to grasping irregular objects where suction-based grasping is impractical and/or impossible.

In an exemplary embodiment, a method for donning a compression garment over a limb comprises providing a sleeve having a first opening, a second opening, an inner surface and an outer surface wherein the first opening, the inner surface and the second opening cooperate to define a passage through the sleeve for a limb, the inner surface and the outer surface being formed of and defined by a continuous flexible material; providing a plurality of longitudinally continuous and parallel raised lines which extend outwardly from the inner surface and the outer surface; providing a fluid within the continuous film of flexible material, the fluid comprising at least one of water, solutions of water, oil, air, foams, urethane, silicone, soap, or lubricant; providing a compression garment having at least one opening at one end thereof; providing a pole extending from a surface, the pole having a diameter equal to or less than the diameter of the passage; providing a strap; centering the strap on the pole opposite the surface, the strap being long enough so that both ends of the strap reach the surface; providing a suction device at one end of the pole, the suction device being adapted to removably affix the pole to the surface; sliding the at least one opening over the pole until the compression garment is fully extended over the pole; placing the second opening on the pole opposite the surface; sliding the sleeve over the pole whereby the continuous film of flexible material everts such that the inner surface becomes the outer surface at the second opening while the outer surface becomes the inner surface at the first opening; pulling the at least one opening into contact with the outer surface at the second opening once the sleeve reaches the at least one opening; lifting the sleeve away from the surface whereby the continuous film of flexible material everts such that the inner surface becomes the outer surface at the first opening while the outer surface becomes the inner surface at the second opening; tucking the at least one opening (and/or any level of the compression garment that is desired for fewer eversions) into the first opening when everting the compression garment off the pole; grasping the ends of the straps and lifting off the pole to cause the compression garment to evert until it is completely removed from the pole, the end of the compression garment opposite the at least one opening abutting the first opening; positioning the first opening over a patient's limb; rolling the sleeve up the patient's limb whereby the inner surface and the outer surface evert thereby leaving the compression garment on the limb; disengaging the at least one opening from the second opening; and rolling the sleeve back down the limb until removed from the limb.

In another exemplary embodiment, a method of doffing a compression garment from a limb comprises providing a sleeve having a first opening, a second opening, an inner surface and an outer surface wherein the first opening, the inner surface and the second opening cooperate to define a passage through the sleeve for a limb, the inner surface and the outer surface being formed of and defined by a continuous flexible material, providing a plurality of longitudinally continuous and parallel raised lines which extend outwardly from the inner surface and the outer surface; providing a fluid within the continuous flexible material, the fluid comprising at least one of water, solutions of water, oil, air, foams, urethane, or silicone; sliding at least one opening over the limb until the compression garment is fully extended over the limb; placing the first opening on the limb; sliding the sleeve over the limb whereby the continuous flexible material everts such that the inner surface becomes the outer surface at the first opening while the outer surface becomes the inner surface at the second opening; pulling the at least one opening into contact with the outer surface at the first opening once the sleeve reaches the at least one opening; tucking the at least one opening into the second opening when everting the compression garment off the limb; and lifting the sleeve away from the surface whereby the continuous flexible material everts such that the inner surface becomes the outer surface at the second opening while the outer surface becomes the inner surface at the first opening, the lifting continuing until the compression garment is completely removed from the limb, the end of the compression garment opposite the at least one opening abutting the second opening. The method may further comprise disengaging the compression garment from the sleeve.

In another exemplary embodiment, a method for donning and doffing a compression garment over a limb comprises providing a sleeve having a first opening, a second opening, an inner surface and an outer surface wherein the first opening, the inner surface and the second opening cooperate to define a passage through the sleeve for a limb, the inner surface and the outer surface being formed of and defined by a continuous flexible material; providing a plurality of longitudinally continuous and parallel raised lines which extend outwardly from the inner surface and the outer surface; providing a fluid within the continuous flexible material, the fluid comprising at least one of water, solutions of water, oil, air, foams, urethane, or silicone; providing a compression garment having at least one opening at one end thereof; providing a pole extending from a surface, the pole having a diameter equal to or less than the diameter of the passage; providing a strap, centering the strap on the pole opposite the surface, the strap being long enough so that both ends of the strap reach the surface; providing a suction device at one end of the pole, the suction device being adapted to removably affix the pole to the surface; sliding the at least one opening over the pole until the compression garment is fully extended over the pole; placing the second opening on the pole opposite the surface; sliding the sleeve over the pole whereby the continuous flexible material everts such that the inner surface becomes the outer surface at the second opening while the outer surface becomes the inner surface at the first opening; pulling the at least one opening into contact with the outer surface at the second opening once the sleeve reaches the at least one opening; lifting the sleeve away from the surface whereby the continuous film of flexible material everts such that the inner surface becomes the outer surface at the first opening while the outer surface becomes the inner surface at the second opening, tucking the at least one opening into the first opening when everting the compression garment off the pole; grasping the ends of the straps and lifting off the pole which causes the compression garment to evert until it is completely removed from the pole, the end of the compression garment opposite the at least one opening abutting the first opening; positioning the first opening over a patient's limb; rolling the sleeve up the patient's limb whereby the inner surface and the outer surface evert thereby leaving the compression garment on the limb; disengaging the at least one opening from the second opening; rolling the sleeve back down the limb until removed from the limb; sliding at least one opening over the limb until the compression garment is fully extended over the limb; placing the first opening on the limb; sliding the sleeve over the limb whereby the continuous flexible material everts such that the inner surface becomes the outer surface at the first opening while the outer surface becomes the inner surface at the second opening; pulling the at least one opening into contact with the outer surface at the first opening once the sleeve reaches the at least one opening; tucking the at least one opening into the second opening when everting the compression garment off the limb; lifting the sleeve away from the surface whereby the continuous flexible material everts such that the inner surface becomes the outer surface at the second opening while the outer surface becomes the inner surface at the first opening, the lifting continuing until the compression garment is completely removed from the limb, the end of the compression garment opposite the at least one opening abutting the second opening; and disengaging the compression garment from the sleeve.

In another exemplary embodiment, a method for donning and doffing a compression garment over a limb comprises providing a sleeve having a first opening, a second opening, an inner surface and an outer surface wherein the first opening, the inner surface and the second opening cooperate to define a passage through the sleeve for a limb, the inner surface and the outer surface being formed of and defined by a continuous flexible material; providing a compression garment having at least one opening at one end thereof; providing a pole extending from a surface, the pole having a diameter equal to or less than the diameter of the passage; sliding the at least one opening over the pole until the compression garment is fully extended over the pole; placing the second opening on the pole opposite the surface; sliding the sleeve over the pole whereby the continuous flexible material everts such that the inner surface becomes the outer surface at the second opening while the outer surface becomes the inner surface at the first opening; pulling the at least one opening into contact with the outer surface at the second opening once the sleeve reaches the at least one opening; lifting the sleeve away from the surface whereby the continuous flexible material everts such that the inner surface becomes the outer surface at the first opening while the outer surface becomes the inner surface at the second opening, the lifting continuing until the compression garment is completely removed from the pole, the end of the compression garment opposite the at least one opening abutting the first opening; positioning the first opening over a patient's limb; rolling the sleeve up the patient's limb whereby the inner surface and the outer surface evert thereby leaving the compression garment on the limb; disengaging the at least one opening from the second opening; rolling the sleeve back down the limb until removed from the limb; sliding the at least one opening over the limb until the compression garment is fully extended over the limb; placing the first opening on the limb, sliding the sleeve over the limb whereby the continuous flexible material everts such that the inner surface becomes the outer surface at the first opening while the outer surface becomes the inner surface at the second opening; pulling the at least one opening into contact with the outer surface at the first opening once the sleeve reaches the at least one opening; and lifting the sleeve away from the surface whereby the continuous flexible material everts such that the inner surface becomes the outer surface at the second opening while the outer surface becomes the inner surface at the first opening, the lifting continuing until the compression garment is completely removed from the limb, the end of the compression garment opposite the at least one opening abutting the second opening.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims.

In the foregoing specification, the disclosure has been described with reference to various embodiments. However, one of ordinary skill in the art appreciates that various modifications and changes can be made without departing from the scope of the present disclosure. Accordingly, the specification is to be regarded in an illustrative rather than a restrictive sense, and all such modifications are intended to be included within the scope of the present disclosure. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims. As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C.

What is claimed is:

1. An apparatus for donning and doffing a compression garment, the apparatus comprising:
   a sleeve configured with a first sleeve opening, a second sleeve opening, an inner surface and an outer surface,
   wherein the first sleeve opening, the inner surface and the second sleeve opening cooperate to define a passage through the sleeve for a limb,
   wherein the inner surface and the outer surface are formed of and defined by a continuous flexible material, and
   wherein the outer surface at the second sleeve opening is configured for contact with at least one opening of the compression garment such that the compression garment can be continuously everted throughout the sleeve until the end of the compression garment opposite the at least one opening abuts the first sleeve opening;
   the apparatus further comprising a pole configured to receive the compression garment.

2. The apparatus of claim 1, further comprising a strap configured to provide a force to evert the sleeve off the pole.

3. An apparatus for donning and doffing a compression garment, the apparatus comprising:
   a sleeve configured with a first sleeve opening, a second sleeve opening, an inner surface and an outer surface,
   wherein the first sleeve opening, the inner surface and the second sleeve opening cooperate to define a passage through the sleeve for a limb,
   wherein the inner surface and the outer surface are formed of and defined by a continuous flexible material,
   wherein the outer surface at the second sleeve opening is configured for contact with at least one opening of the compression garment such that the compression garment can be continuously everted throughout the sleeve until the end of the compression garment opposite the at least one opening abuts the first sleeve opening; and
   wherein the sleeve is filled with at least one of powder, petroleum jelly, or glass beads.

4. The apparatus of claim 2, wherein the pole extends a length longer than the compression garment, and wherein the strap is at least twice the length of the pole.

5. An apparatus for donning and doffing a compression garment, the apparatus comprising:
   a sleeve configured with a first sleeve opening, a second sleeve opening, an inner surface and an outer surface,
   wherein the first sleeve opening, the inner surface and the second sleeve opening cooperate to define a passage through the sleeve for a limb,
   wherein the inner surface and the outer surface are formed of and defined by a continuous flexible material,
   wherein the outer surface at the second sleeve opening is configured for contact with at least one opening of the compression garment such that the compression garment can be continuously everted throughout the sleeve until the end of the compression garment opposite the at least one opening abuts the first sleeve opening; and
   wherein the sleeve is configured with a plurality of raised lines extending from the inner surface and the outer surface.

6. A method for coupling a sleeve and a compression garment, the method comprising:
   placing a compression garment over a pole;
   everting a sleeve in a first direction along the pole such that the compression garment is located between the sleeve and the pole;
   tucking an end of the compression garment into the sleeve; and
   everting the sleeve along the pole in a second direction opposite the first direction to cause the compression garment to wrap around the sleeve; and
   wherein the sleeve is filled with a fluid.

7. The method of claim 6, wherein the everting the sleeve along the pole in the second direction is accomplished via a strap disposed between the compression garment and the pole.

8. A method for donning a compression garment, the method comprising:
- providing a sleeve having a first sleeve opening, a second sleeve opening, an inner surface and an outer surface wherein the first sleeve opening, the inner surface and the second sleeve opening cooperate to define a passage through the sleeve for a limb, the inner surface and the outer surface being formed of a continuous flexible material,
- providing a compression garment having at least one opening at one end thereof;
- providing a pole extending from a surface;
- sliding the at least one opening over the pole until the compression garment is fully extended over the pole;
- placing the second sleeve opening on the pole opposite the surface,
- sliding the sleeve over the pole whereby the continuous flexible material everts such that the inner surface becomes the outer surface at the second opening while the outer surface becomes the inner surface at the first opening;
- pulling the at least one opening into contact with the outer surface at the second sleeve opening once the sleeve reaches the at least one opening;
- lifting the sleeve away from the surface whereby the continuous flexible material everts such that the inner surface becomes the outer surface at the first opening while the outer surface becomes the inner surface at the second opening, the lifting continuing until the compression garment is completely removed from the pole, the end of the compression garment opposite the at least one opening abutting the first opening;
- positioning the first sleeve opening over a patient's limb;
- rolling the sleeve up the patient's limb whereby the inner surface and the outer surface evert thereby leaving the compression garment on the limb;
- disengaging the at least one opening from the second sleeve opening; and
- rolling the sleeve back down the limb until removed from the limb.

9. The method of claim 8, wherein the sleeve comprises a plurality of longitudinally continuous and parallel raised lines which extend outwardly from the inner surface and the outer surface.

10. The method of claim 8, wherein the sleeve comprises a fluid within the sleeve.

11. The method of claim 10, wherein the fluid is at least one of water, solutions of water, oil, air, foams, urethane, silicone, soap or lubricant.

12. The method of claim 8, wherein the pole further comprises a base mount at one end of the pole, the base mount configured to removably affix the pole to the surface.

13. The method of claim 8, further comprising tucking the at least one opening into the first sleeve opening when everting the compression garment off the pole.

14. The method of claim 8, further comprising:
- placing a strap on the pole opposite the surface, the strap being long enough so that both ends of the strap extend from the at least one opening after the compression garment is positioned on the pole; and
- grasping the ends of the straps and applying a force to cause the compression garment to evert until it is removed from the pole.

15. The method of claim 14, wherein the strap is coupled to the pole via a fastener.

* * * * *